United States Patent [19]
Fogel

[11] Patent Number: 5,866,585
[45] Date of Patent: Feb. 2, 1999

[54] METHODS OF TREATING TARDIVE DYSKINESIA USING NMDA RECEPTOR ANTAGONISTS

[75] Inventor: Barry S. Fogel, Providence, R.I.

[73] Assignee: Synchroneuron, LLC, Waban, Mass.

[21] Appl. No.: 861,801

[22] Filed: May 22, 1997

[51] Int. Cl.⁶ .......................... A61K 31/13; A61K 31/44
[52] U.S. Cl. .......................................... 514/289; 514/662
[58] Field of Search ...................................... 514/289, 662

[56] References Cited

U.S. PATENT DOCUMENTS

| | | |
|---|---|---|
| 4,122,193 | 10/1978 | Scherm et al. ............................ 426/330 |
| 5,061,703 | 10/1991 | Bormann et al. . |
| 5,262,162 | 11/1993 | Bormann et al. . |
| 5,382,601 | 1/1995 | Nürnberg et al. . |
| 5,455,279 | 10/1995 | Lipton . |
| 5,614,560 | 3/1997 | Lipton . |

OTHER PUBLICATIONS

Trube et al. Epilepsia (N.Y.), 35(Suppl. 5), 562–67 (Abstract), 1994.
Andreacsen et al. (Abstract) Br. J. of Pharm. 19(4)751–7, Oct. 1960.
Andrew, "Clinical Relationship of Extrapyramidal Symptoms and Tardive Dyskinesia", Can. J. Psych., 39:576–580, 1994.
Bezchilbynk–Butler et al., "Antiparkinsonian Drugs in the Treatment of Neuroleptic–Induced Extrapyramidal Symptoms", Can. J. Psych., 39:74–84, 1994.
Boumans et al., "Is the Social Acceptability of Psychiatric Patients Decreased by Orofacial Dyskinesia?", Schizo Bull, 20:339–344, 1994.
Buchel et al., "Oral Tardive Dyskinesia: Validation of a Measuring Device Using Digital Image Processing", Psychopharmacology–Berl, 117:162–165, 1995.
Chakos et al., "Incidence and Correlates of Tardive Dyskinesia in First Episode of Schizophrenia", Arch Gen Psychiatry, 53:313–319, 1996.
Deckes et al., "Amantadine Hydrochloride Treatment of Tardive Dyskinesia", Oct. 7, New England J. Med, 285:860, 1971.
Delfs et al., "Expression of Glutamic Acid Decarboxylase mRNA in Striatum and Pallidum in an Animal Model of Tardive Dyskinesia", Exp. Neurol, 133:175–188, 1995.
Dimpfel, "Effects of Memantine on Synaptic Transmission in the Hippocampus in Vitro", Arzneimittelforschung, 45:1–5, 1995.
Erdo et al., "Memantine is Highly Potent in Protecting Cortical Cultures against Excitotoxic Cell Death Evoked by Glutamate and N–Methyl–D–Aspartate", Eur. J. Pharmacol, 198:215–217, 1991.
Gao et al., "Tiagabine Inhibits Haloperidol–Induced Oral Dyskinesias in Rats", J. Neural Transmission, 95:63–69, 1994.
Hayashi et al., "Prevalence of and Risk Factors for Respiratory Dyskinesia", Clin. Neuropharmacol, 19:390–398, 1996.
Imamura et al., "Improved Preservation with Amantadine", Abstract, No–To–Shinkei, 46:556–562, 1994.
Jeste et al., "Risk of Tardive Dyskinesia in Older Patients. A Prospective Longitudinal Study of 266 Outpatients", Arch Gen Psychiatry, 52:756–765, 1995.
Keilhoff et al., "Memantine Prevents Quinolinic Acid–Induced Hippocampal Damage", Eur. J. Pharmacol, 219:451–454, 1992.
Kornhuber et al., "New Therapeutic Possibilities with Low–Affinity NMDA Receptor Antagonists", Abstract, Nervenarzt, 67:77–82, 1996.
Lam et al., Vitamin E in the Treatment of Tardive Dyskinesia: A Replication Study, J. Nerv. Ment Dis, 182:113–114, 1994.
Latimer, "Tardive Dyskinesia: A Review", Abstract, Can J. Psych, 40:S49–54, 1995.
Lohr et al., "A Double–Blind Placebo–Controlled Study of Vitamin E Treatment of Tardive Dyskinesia", J. Clin. Psychiatry, 57:167–173, 1996.
Muller et al., "Noncompetitive NMDA Receptor Antagonists with Fast Open–Channel Blocking Kinetics and Strong Voltage–Dependency as Potential Therapeutic Agents for Alzheimer's Dementia", Pharmacopsychiatry, 28:113–124, 1995.
Pahl et al., "Positron–Emission Tomography in Tardive Dyskinesia", J. Neuropsych Clin. Neurosci, 7:457–465, 1995.
Raja, "The Treatment of Tardive Dyskinesia", Abstract, Schweiz Arch Neurol Psychaitr, 47:13–18, 1996.
Sachdev et al., "Negative Symptoms, Cognitive Dysfunction, Tardive Akathisia and Tardive Dyskinesia", Acta Psychiatr Scand, 93:451–459, 1996.
Sano et al., "A Controlled Trial of Selegiline, Alpha–Tocopherol, or Both as Treatment for Alzheimer's Disease", The New England Journal of Medicine, vol. 336, No. 17, pp. 1216–1247, Apr. 24, 1997.

(List continued on next page.)

*Primary Examiner*—Leonard Schenkman
*Attorney, Agent, or Firm*—Choate, Hall & Stewart

[57] ABSTRACT

A method for treating symptoms of patients diagnosed with tardive dyskinesia (TD) using NMDA receptor antagonists is disclosed. This invention illustrates that certain NMDA-receptor antagonists are effective pharmacologic agents in the treatment of hyperkinesia and cognitive disorders that present in patients diagnosed with TD. The disclosed agents reduce the severity and duration of involuntary movements associated with tardive dyskinesia. Certain of the disclosed agents are also effective in increasing the attention span, concentration span, memory and everyday functional performance as measured both subjectively as well as objectively as demonstrated using standard neuropsychological tests such as those assessing reaction time and short-term memory. The invention also discloses a method of treating tardive dyskinesia that acts in a neuroprotective manner to reduce or prevent glutamate-related excitotoxic damage to the basal ganglia.

6 Claims, No Drawings

OTHER PUBLICATIONS

Schulz et al., "Neuroprotective Strategies for Treatment of Lesions Produced by Mitochondrial Toxins: Implications for Neurodegenerative Diseases", Neuroscience, 71:1043–1048, 1996.

Silver et al., "No Difference in the Effect of Biperiden and Amantadine on Parkinsonian– and Tardive Dyskinesia–type Involuntary Movements: A Double–Blind Crossover, Placebo–Controlled Study in Medicated Chronic Schizophrenic Patients", Abstract, J. Clin. Psychiatry, 56:167–170, 1995.

Stoessl, "Effects of Ethanol in a Putative Rodent Model of Tardive Dyskinesia", Pharmacol Biochem Behav, 54:541–546, 1996.

Swartz, "Tardive Psychopathology", Neuropsychobiology, 43:115–119, 1995.

Tirelli et al., "Differential Effects of Direct and Indirect Dopamine Agonists on the Induction of Gnawing in C57B1/6J Mice", J. Pharmacol Exp. Ther., 273:7–15, 1995.

Vale et al., "Amantadine for Dyskinesia Tarda", New Eng. J. Med., 284:673, 1971.

Van–Rekum et al., "N of 1 Study: Amantadine for the Amotivational Syndrome in a Patient with Traumatic Brain Injury", Brian Inj. 9:49–53, 1995.

Waddington et al., "Cognitive Dysfunction in Chronic Schizophrenia Followed Prospectively Over 10 Years and Its Longitudinal Relationship to the Emergence of Tardive Dyskinesia", Psychol Med, 26:681–688, 1996.

Wenk et al., "MK–801, Memantine and Amantadine Show Neuroprotective Activity in the Nucleus Basalis Magnocellularis", Eur. J. Pharmacol, 293:267–270, 1995.

METHODS OF TREATING TARDIVE DYSKINESIA USING NMDA RECEPTOR ANTAGONISTS

BACKGROUND OF THE INVENTION

Tardive dyskinesia (TD) is a chronic disorder of the nervous system, characterized by involuntary jerky movements of the mouth, tongue, and facial muscles. In severe cases, TD may be characterized by wormlike (athetoid) movements of the extremities resulting in a drunken-appearing gait. The disorder is an extrapyramidal movement disorder associated with prolonged use of antipsychotic (neuroleptic) drugs. TD may manifest or worsen in severity even after a patient ceases use of neuroleptic agents. TD may become irreversible despite cessation of neuroleptic treatment.

The cumulative incidence of TD in patients exhibiting a first episode of schizophrenia who have undergone a four-year course of neuroleptic treatment is 16.5% (Chakos et al., *Arch. Gen. Psychiatry* 53:313,1996). The cumulative incidence is substantially higher in older people and in those being treated for conditions other than schizophrenia (see, e.g., Hayashi et al., *Clin Neuropharmacol* 19:390, 1996; Jeste et al., *Arch. Gen. Psychiatry* 52:756, 1995).

Other extrapyramidal syndromes associated with prolonged use of neuroleptics include dystonias, drug-induced parkinsonianism (as opposed to the idiopathic variety) and akathisia or akinesia. Cognitive disorders are also associated with tardive dyskinesia, and may include impairment in attention, concentration, or other cognitive functions (see, e.g., Sachdev et al., *Acta Psychiatr Scand* 93:451, 1996; Waddington & Youssef, *Psychol Med.* 26:681, 1996; Swartz, *Neuropsychobiology* 32:115, 1995).

While the pathophysiologic mechanism of tardive dyskinesia is unknown, there is speculation that chronic or prolonged administration of neuroleptics, which act by blocking dopamine receptors (e.g., amoxapine, chlorpromazine, fluphenazine, halopridol, one notable exception being clozapine), results in hypersensitivity or up-regulation of dopamine receptors in the basal ganglia of the brain (see e.g., Andrews, *Can J Psych* 39:576, 1994; Casey, D. E. in *Psychopharmacology: The Fourth Generation of Progress,* Raven Press, 1995). Drugs that increase or enhance dopamine response, especially indirect dopamine agonists, can aggravate the disorder. Many psychiatrists avoid using dopamine agonist anti-Parkinson drugs in neuroleptic therapy because of a concern that increased dopamine will aggravate tardive dyskinesia. (Bezchibnyk-Butler & Remington, *Can J. Psych.* 39:74, 1994).

Glutamate-related excitotoxic damage to the basal ganglia has also been suggested as a potential cause of irreversible tardive dyskinesia (Andreasen & Jorgensen 1994).

While recent research suggest that Vitamin E can reduce symptoms of the disorder modestly (Lohr & Caliguiri, *J Clin Psychiatry* 57;167, 1996; Dabiri et al. 1994), there is no generally accepted treatment for either the movement or cognitive disorders associated with TD.

Memantine is a drug approved in Europe for treatment of Parkinson's disease. Memantine, a congener of amantadine, is a N-methyl-D-aspartate type (NMDA) receptor antagonist as well as a dopamine agonist. Although memantine has been reported to alleviate some of the dyskinetic movements that can be seen in treated Parkinson's disease, there are no reports of its use in humans to treat tardive dyskinesia, and at least one notable expert in the field of TD has expressed surprise that any anti-Parkinson's drug would be an effective agent against TD (Jeste, pers. comm.).

In U.S. Pat. No. 4,122,193, it is reported that 1,3,5-trisubstituted adamantane, including 1-amino-3,5-dimethyl-adamantane is useful in the treatment of hyperkinesis in rats. The agent is also recommended as a treatment generally for hyperkinesis, albeit in the context of Parkinson's as well as head tremors, thalmic tension conditions and spastic conditions, and for the activation of akinetic cerebroorganic conditions. It is notable that, unlike TD, these conditions are not thought to be aggravated by dopamine agonists. Moreover, there is no recognition in the reference that 1-amino-3,5-dimethyl-adamantane acts as a NMDA-receptor antagonist. Instead, disclosure indicates that 1,3,5-trisubstituted adamantane compounds "influence catecholamine metabolism, for instance by freeing dopamine or stimulating the receptors". This latter aspect suggests that the authors did not recognize that memantine could be an effective treatment of TD, for which administration of a dopamine agonist goes against expert opinion.

An object of this invention is to develop methods for treating tardive dyskinesia using NMDA receptor antagonists. Another object of this invention to develop new methods to treat hyperkinesia associated with tardive dyskinesia. More particularly, it is an object of the invention to reduce the severity and duration of involuntary movements associated with tardive dyskinesia. More particularly, it is the object of this invention to develop methods of treating tardive dyskinesia which utilize NMDA-receptor antagonists as a therapeutic approach.

Another object of the invention is to develop new methods for improving cognitive function in patients exhibiting TD, specifically to increase the attention span, concentration span, memory and everyday functional performance as measured both subjectively and objectively. The latter may be demonstrated using standard neuropsychological tests such as those assessing reaction time and short-term memory.

Another object of the invention is to develop new methods of treating tardive dyskinesia that act in a neuroprotective manner to reduce or prevent glutamate-related excitotoxic damage to the basal ganglia.

SUMMARY OF THE INVENTION

The invention relates to a method of treating tardive dyskinesia in humans. In one aspect, the invention reduces involuntary movements or hyperkinesia characteristic of patients with tardive movement disorders, including tardive dyskinesia, by the administration of a pharmacological agent that has a blocking effect on NMDA receptors. Such pharmacological agents may also be dopamine agonists.

In relation to the first aspect of the invention, I have discovered that certain agents used in the treatment of Parkinson's disease, thought unsuitable for use in treatment of tardive dyskinesia, are effective in reducing the hyperkinesia of patients with TD. Several years ago, I hypothesized that TD represents a form of non-linear oscillation in neural circuits involving the basal ganglia, and that that oscillation might be reduced by agents that block excitatory neurotransmission. Subsequently, evidence from PET scans documented increased metabolism in the globus pallidus and primary motor cortex in schizophrenic patients with TD, but not in those without TD (Pahl et al., *J Neuropsych Clin Neurosci* 7:457, 1995).

Additional support for my hypothesis that a method of treatment for TD and its related hyperkinesia, cognitive functioning and excitotoxic-related neural damage could be effective as a result of reducing the gain in a circuit through the striatum comes from animal evidence that agents that directly or indirectly stimulate GABA receptors can decrease neuroleptic-induced dyskinesias (Stoessl, *Pharmacol Biochem Behav* 54:541, 1996; Gao et al. *J Neural Transmission* 95:63, 1993). (GABA is an inhibitory neurotransmitter and is found in the striatum). Rats with neuroleptic-induced dyskinesia demonstrate decreased striatal levels of glutamic acid decarboxylase, the rate limiting enzyme in the production of GABA (Delfs et al., *Exp Neurol* 133:175, 1995).

Without limiting the biochemical mechanism of the invention to that described here, it appears that drugs that act to reduce the gain in the hypothesized oscillator circuit would reduce the involuntary movements of tardive dyskinesia. Generally, antagonists of excitatory neurotransmitters such as glutamate came into consideration, although other agents such as GABA agonists may be obvious to one skilled in the art.

In one preferred embodiment of this aspect of the invention, a pharmaceutical agent is selected from the group of agents that act as NMDA receptor antagonists such as, in a non-limiting fashion, dextromethorphan, memantine, or congeners or derivatives thereof. In another preferred embodiment, a pharmaceutical agent is selected from the group of agents that have the ability to reduce excitatory post-synaptic potentials in striatal cells induced by glutamate, such as, in a non-limiting fashion, dextromethorphan, memantine, amantadine, or congeners or derivatives thereof.

A second aspect of the invention features a method of improving cognitive function in humans with tardive dyskinesia as demonstrated by performance in neuropsychological tests, including without limitation measurements of Simple Reaction Time, Choice Reaction Time, PASAT, Digit Symbol, Figural Fluency, the Boston Qualitative Scoring System for the Rey-Osterrieth Complex Figure, and California Verbal Learning Test as well as demonstrated by subjective indicators. It will be obvious to one skilled in the art that other neuropsycological tests could be employed.

A third aspect of the invention features a method of treating tardive dyskinesia that has neuroprotective qualities. "Neuroprotective" means that administration of memantine or other NMDA-glutamate receptor antagonists has a protective effect against glutamate-related excitotoxic damage to the basal ganglia.

DETAILED DESCRIPTION OF PREFERRED EMBODIMENTS

NMDA receptor antagonists can be used according to the method of the invention to reduce the severity of hyperkinesia associated with tardive dyskinesia. Moreover, NMDA receptor antagonists can mitigate the onset and severity of cognitive disorders associated with TD, while providing neuroprotective properties.

Generally, the method of the invention can be used for the treatment of tardive dyskinesia, including the treatment of the hyperkinesia, cognitive disorders and excitotoxic-related neurological damage associated with the disorder.

The method relates to the administration of an effective dose of a NMDA-receptor antagonist chosen from among a group of NMDA-receptor antagonists that include, in a non-limiting fashion, dextromethorphan, memantine, and congeners or derivatives thereof.

Memantine is a NMDA antagonist that is also a dopamine agonist. Furthermore, memantine is a congener of amantadine, a widely-used antiparkinson drug. Amantadine like memantine is a NMDA-receptor antagonist and an indirect dopamine agonist but it is a much weaker NMDA receptor antagonist than memantine. Although it has been reported to have some mild ameliorative effects on TD in patients who are also receiving neuroleptics, amantadine has not been reported as a treatment of TD in patients not concurrently receiving neuroleptics.

Amantadine has been used with mixed results as a treatment of cognitive dysfunction, fatigue and apathy in other non-TD-related neurologic diseases, including individuals with brain damage. In a controlled study, however, it was not demonstrated to enhance cognitive function in patients with multiple sclerosis (Geisler et al. 1996).

Dextromethorphan, like memantine and amantadine, is a NMDA receptor antagonist. There have been no reports of its use in the treatment of dyskinesia.

In the method of the claimed invention, "NMDA-receptor antagonist" and/or "NMDA glutamate receptor antagonist" refers to molecules that are capable of binding to active or modulatory sites on the NMDA receptor.

In the method of the claimed invention, "effective" dose refers to one that is administered in doses tailored to each individual patient manifesting symptoms of tardive dyskinesia sufficient to cause a reduction in the associated hyperkinesia or an improvement in the associated cognitive disorders with tolerable adverse effects. Experimentally, doses of memantine ranging from 10 mg to 30 mg have been shown to be effective, and of dextromethorphan ranging from 30 mg four times a day to 60 mg four times a day, but a person skilled in the art will recognize that treatment of patients with pharmaceutical agents must be tailored to the invididual patient, taking into account height, weight, severity of symptoms and stage of the disorder to be treated.

The following case report illustrates the preferred method of the invention:

Case report

1. General.

A 44-year old woman, known here as Patient Anna, presented for treatment with severe involuntary movements. These irregularly-rhythmic movements consisted of forced eye blinking (blepharospasm), thrusting of the tongue forward and from side to side, tongue twisting, grimacing, shoulder shrugging, and tensing of the platysma muscles of the neck. Patient Anna is a semi-professional musician; the dykinetic movements were accompanied by significant occupational disability, including difficulty reading music or text and difficulty playing woodwind instruments. She had impaired attention, concentration and memory compared with her performance before onset of TD. She had significant fatigue, and usually required rest in bed at some point during each day. The patient was diagnosed with TD by a Board-certified neurologist with extensive experience in evaluating neuroleptic-induced side effects.

The involuntary movements developed during a 6-year course of treatment with amoxapine, an antidepressant drug with known neuroleptic properties, between 1982 and 1988. Hyperkinesia worsened after the amoxapine was discontinued. Palliative treatment with alprazolam (an anxiolytic; 0.25 mg four times a day) and trihexyphenidyl (an anticholinergic; 2 mg twice a day) was given by another physician, resulting in minimal improvement. Patient Anna began treatment with me in the winter of 1992 and was maintained on trihexyphenidyl for an additional 18 months. Trihexyphenidyl was then discontinued without a change in her involuntary movements. During 1993, alprazolam was increased to 0.5 mg four times a day, to treat mild symptoms of anxiety; the change in dosage had no detectable effect on the patient's involuntary movements.

Treatment trials with buspirone, sertraline, verapamil, and vitamin E in 1992 either produced little benefit or were not tolerated at doses that slightly reduced her involuntary movements. None of these drugs significantly improved the patient's everyday function, i.e., her performance at reading text or music, her stamina and her ability to concentrate. The first drug that provided significant and sustained benefits was nimodipine, a cerebroselective calcium channel blocker, which, beginning in 1993, was administered in a regime that included 30 mg of nimodipine four times a day. This regime reduced Anna's hyperkinesia by about 50% but she experienced adverse effects, including dizziness, lightheadedness, and palpitations and had no symptomatic improvement in cognitive function. There was a meaningful improvement in her ability to read and to play music. The efficacy of the therapy with nimodipine was demonstrated by stopping and restarting the drug. Movements increased within 24 hours of discontinuation and decreased within 24 hours of reinstitution of the drug.

2. Hyperkinesia.

In 1995, memantine came to my attention as a relatively non-toxic NMDA receptor antagonist. In view of my hypothesis about the pathophysiology of tardive dyskinesia, I thought that memantine might be beneficial in its treatment. Nimodipine was discontinued, and the patient was begun on memantine using a regime of 10 mg twice a day. The hyperkinetic movements associated with TD were reduced within 24 hours of administration of memantime, to a substantially greater degree than was observed with nimodipine. Adverse effects included a sense of mild intoxication. Adjustments to the therapeutic regime were made such that the drug was reduced to 5 mg three times a day, with the result that the therapeutic benefits were maintained without perceptible side effects. In addition, the patient reported improved energy, attention, and concentration.

Administration of a NMDA-receptor antagonist such as memantine was found to be effective in reducing the hyperkinesia associated with TD, while showing a demonstrable improvement in cognitive function. The effectiveness of the method of the invention for reducing the movements of TD is documented in Table 1, in which severity of the movement disorder is assessed while the patient is both on and off the drug.

TABLE 1

Movement on and off memantine

| Movement | On Memantine | Off Memantine |
|---|---|---|
| Shoulder shrugging | 0 | 1 |
| Tensing of platysma | 0 | 1 |
| Grimacing | 1 | 2 |
| Neck Stiffening | 1 | 2 |
| Eye closure | 1 | 2 |
| Tongue movements | 1 | 2 |

(Severity is measured on a scale of 0 to 3:
0-absent 1-mild 2-moderate 3-severe.)

Subjectively, Patient Anna reported that her everyday function was improved to a greater extent during treatment with memantine than that experienced during treatment with nimodipine. She was able to read or to play her instrument for longer periods with less of a need for rest during the day. Objectively, Anna's cognitive functioning, including attention span, concentration span and memory improved as indicated by neuropsychological testing.

3. Cognitive Function.

Neuropsychological tests were administered to the patient on and off memantine. The first test administration was during a period when she was undergoing treatment with memantine, in order minimize spurious benefits due to learning effects. The neuropsychological test results indicate that memantine therapy was associated with significant improvements in verbal learning, psychomotor speed (reaction time), and visuospatial performance. Subsequent testing over a two-year course of treatment with memantine confirmed that these improvements were not only maintained over time but were also accompanied by a gradual additional reduction in the hyperkinesia.

Given the patient's reluctance to participate in a prolonged neuropsychological evaluation, particularly without medication, test batteries were kept brief and limited to assessment of reaction time, mental processing speed, psychomotor speed, executive functioning, visuospatial skills, and memory functioning. Given both the non-blind condition of the examinations (for both patient and examiner) and possible practice effects, tests were selected which have been shown to be less sensitive to subjective performance variables (e.g., exaggeration of deficits) and to practice effects.

Table 2 indicates that, during the on-drug examination, Patient Anna exhibited more rapid simple reaction times (SRT), faster cognitively-mediated choice reaction times (CRT), and markedly better psychomotor speed (as evidenced on the Digit Symbol test). Information processing speed (PASAT) remained largely unchanged. With regard to executive functioning, treatment with memantine resulted in improved performance on the Figural Fluency Test, which tests one's ability to generate unique visual designs rapidly. Visiospatial performance (Complex Figure Test) appeared relatively better, or the same, on-drug. Delayed Retention of Complex Figure indicated somewhat better delayed recall off drug. Assessment of verbal memory functioning (the California Verbal Learning Test (CVLT)) showed that the patient performed better on the drug across all parameters of learning and memory. Large differences were noted between the total words recalled over learning trials 1–5, short- and long- delay free and cued recalls, and recognition; in all cases, her performance was better while on-drug.

In summary, the patient was administered a focused battery of neuropsychological tests 45 days apart, with the first session on-drug and the second session off-drug. The medication was associated with better performance across several neuropsychological tests, including measures of reaction time, psychomotor speed, figural fluency, and verbal learning and recall. In general, the profile of neuropsychological performance is indicative of an overall neurocognitive "activation."

TABLE 2

| Test/Condition | On-Drug 2/23/96 Raw Score | Scaled Score | Off-Drug 4/8/96 Raw Score | Scaled Score |
|---|---|---|---|---|
| Simple Reaction Time[1] | | | | |
| 1500 Green | 212 msec | NA | 332 msec | NA |
| 1500 Red | 224 msec | NA | 276 msec | NA |
| 500 Green | 284 msec | NA | 343 msec | NA |
| 500 Red | 266 msec | NA | 382 msec | NA |
| Choice Reaction Time[1] | | | | |
| 1500 Green | 365 msec | NA | 542 msec | NA |
| 1500 Red | 422 msec | NA | 643 msec | NA |

TABLE 2-continued

| Test/Condition | On-Drug Raw Score | 2/23/96 Scaled Score | Off-Drug Raw Score | 4/8/96 Scaled Score |
|---|---|---|---|---|
| 500 Green | 362 msec | NA | 603 msec | NA |
| 500 Red | 421 msec | NA | 557 msec | NA |
| PASAT[2] | | | | |
| 2.4 sec ISI Errors | 13 | 96 | 15 | 93 |
| 2.0 sec ISI Errors | 17 | 97 | 21 | 90 |
| 1.6 sec ISI Errors | 21 | 96 | 22 | 94 |
| 1.2 sec ISI Errors | 28 | 94 | 25 | 99 |
| Digit Symbol[3] | 34 | 80 | 20 | 49 |
| Figural Fluency[4] | | | | |
| Unique Designs | 124 | 117 | 99 | 94 |
| Perseverations | 8 | 103 | 4 | 106 |
| Boston Quality Scoring System for the Rey-Osterrieth Complex Figure[5] | | | | |
| Copy Presence & Accuracy | 20 | NA | 17 | NA |
| Copy Organization | 5 | NA | 4 | NA |
| Immediate Retention | −55 | NA | −47.1 | NA |
| Delayed Retention | −11.1 | NA | 22.2 | NA |
| California Verbal Learning Test[6] | | | | |
| List A Trials 1–5 | 53 | 81 | 40 | 54 |
| Short-Delay Free | 10 | 85 | 04 | 40 |
| Long-Delay Free | 12 | 85 | 07 | 55 |
| Recognition (Hits) | 16 | 115 | 14 | 85 |
| False Positives | 03 | 85 | 00 | 100 |
| Intrusions | 3 | 85 | 00 | 115 |

Note: Italicized raw scores are used when higher numbers indicate better performance. In all cases, higher Scaled Scores indicate better performance. Scaled Scores based on available normative data; X = 100, SD = 15.
The following references further describe the tests listed above, and are incorporated herein by reference:
[1] Martin, E. M., Sorensen, D. J., Edelstein, H. E., Robertson, L. C. (1992). Decision-making speed in HIV-1 infection: A preliminary report. AIDS, 6, 109–113;
[2] Gronwall, D. M. A., & Sampson, H. (1977). Paced auditory serial-addition task: A measure of recovery from concussion. Perceptual and Motor Skills, 44, 367–373;
[3] Weschler, D. (1981). WAIS-R Manual. New York: The Psychological Corporation;
[4] Ruff, R. M., Light, R. H., & Evans, R. W. (1987). The Ruff Figural Fluency Test: A normative study with adults. Developmental Neuropsychology, 3, 37–52;
[5] Stern, R. A., Singer, E. A., Duke, L. M., Singer, N. G., Morey, C. E., Daughtrey, E. W., & Kaplan, E. (1994). The Boston Qualitative Scoring System for the Rey-Osterrieth Complex Figure: Description and interrater reliability. The Clinical Neuropsychologist, 8(3), 309–322;
[6] Delis, D. C., Kramer, J. H., Kaplan, E., & Ober, B. A. (1987). The California Verbal Learning Test: Research Edition. New York: The Psychological Corporation.

Discontinuation of memantine resulted in obviously increased dyskinesia within 24 hours, to the point that the movements interfered with reading and musical activities, and caused the patient subjective distress. After re-starting memantine, involuntary movements were reduced to their previous on-treatment level within 24 hours.

The patient's excellent response to memantine supported my hypothesis that NMDA-receptor antagonists might be helpful in tardive dyskinesia. To further that hypothesis, Patient Anna was treated with dextromethorphan, an NMDA-receptor antagonist thought to act at a different site on the NMDA receptor than that observed with memantime. Moreover, dextromethorphan is not a dopamine agonist like memantine or amantadine. Memantime was discontinued and the patient was started on a regime of dextromethorphan administration (30 mg, four times a day). Within 24 hours, the Patient's dyskinetic involuntary movements were reduced to levels seen while the Patient was on memantine. However, the patient felt sedated, and felt that her attention span was shorter and her concentration worse than that experienced while on memantine. Administation of dextromethorphan was continued for one week and reduction of the involuntary movements continued throughout this period. Increased dyskinesia was seen shortly after discontinuation of dextromethorphan administration. Again, memantine was administered, with the result that the dyskinetic movements were reduced to the same extent as during the previous adminstration of memantine.

One aspect of the method of the invention features improvments in the cognitive disorder associated with TD. The improvement in cognition and everyday functional performance seen during the treatment of TD, makes memantine particularly attractive for patients experiencing the cognitive impairment that may accompany TD. Moreover, the fact that memantine is also a dopamine agonist makes memantine and similarly-active congeners particularly suitable for treatment of patients who experience both TD and drug-induced Parkinson's disease.

I envision that additional tests of the effectiveness of NMDA-receptor antagonists will be implemented on an open-end study of 20 patients with severe to extremely severe TD over 12-weeks, with assessment for reduction in the incidence of hyperkinesia and for improvement in cognitive function.

Based on the forgoing, what I claim is the following:

1. A method of treating symptoms of tardive dyskinesia in a subject comprising;
   administering to said subject a NMDA-receptor antagonist selected from the group consisting of dextromethorphan and memantine.

2. The method of claim 1 wherein the symptoms of tardive dyskinesia include impaired cognitive response.

3. The method of claim 1, wherein said symptoms comprise irregular involuntary movements.

4. A method for treating symptoms of neuroleptic-induced tardive movement disorders in a subject comprising:
   administering to said subject a NMDA glutamate receptor antagonist selected from the group consisting of dextromethorphan and memantine.

5. The method of claim 4 wherein one of the symptoms is impaired cognitive response.

6. The method of claim 4 wherein one of the symptoms is involuntary muscular movements.

* * * * *